United States Patent
Kalafut et al.

(10) Patent No.: US 7,674,244 B2
(45) Date of Patent: Mar. 9, 2010

(54) DEVICES, SYSTEMS AND METHODS FOR DETECTING INCREASE FLUID LEVELS IN TISSUE

(75) Inventors: John Kalafut, Pittsburgh, PA (US); Guy Ezekiel, Pittsburgh, PA (US)

(73) Assignee: MEDRAD, Inc., Indianola, PA (US)

( * ) Notice: Subject to any disclaimer, the term of this patent is extended or adjusted under 35 U.S.C. 154(b) by 301 days.

(21) Appl. No.: 11/419,821

(22) Filed: May 23, 2006

(65) Prior Publication Data

US 2007/0276327 A1    Nov. 29, 2007

(51) Int. Cl.
  A61M 1/00  (2006.01)
  A61B 6/00  (2006.01)

(52) U.S. Cl. ...................... 604/151; 600/431

(58) Field of Classification Search ............... 600/431, 600/432; 604/65, 67, 151, 131, 155
  See application file for complete search history.

(56) References Cited

U.S. PATENT DOCUMENTS

| | | | |
|---|---|---|---|
| 4,647,281 A | 3/1987 | Carr | |
| 4,877,034 A * | 10/1989 | Atkins et al. | 600/475 |
| 5,334,141 A | 8/1994 | Carr et al. | |
| 5,494,036 A | 2/1996 | Uber, III et al. | |
| 5,947,910 A | 9/1999 | Zimmet | |
| 5,954,668 A | 9/1999 | Uber, III et al. | |
| 5,964,703 A | 10/1999 | Goodman et al. | |
| 6,339,718 B1 | 1/2002 | Zatezalo et al. | |
| 6,375,624 B1 | 4/2002 | Uber, III et al. | |
| 6,408,204 B1 | 6/2002 | Hirschman | |
| 6,425,878 B1 | 7/2002 | Shekalim | |
| 6,459,931 B1 | 10/2002 | Hirschman | |
| 6,487,428 B1 | 11/2002 | Culver et al. | |
| 6,643,537 B1 | 11/2003 | Zatezalo et al. | |
| 6,751,500 B2 | 6/2004 | Hirschman | |
| RE38,695 E | 2/2005 | Goodman | |
| 6,958,053 B1 | 10/2005 | Reilly | |
| RE38,879 E | 11/2005 | Goodman et al. | |
| 2002/0172323 A1 | 11/2002 | Karellas et al. | |
| 2002/0183613 A1 | 12/2002 | Liu et al. | |
| 2002/0183616 A1 * | 12/2002 | Toews et al. | 600/432 |
| 2003/0004433 A1 | 1/2003 | Hirschman | |

(Continued)

FOREIGN PATENT DOCUMENTS

WO  03009752  2/2003

(Continued)

*Primary Examiner*—Kevin C Sirmons
*Assistant Examiner*—Elizabeth R Moulton
(74) *Attorney, Agent, or Firm*—Jill Denesvich; Henry E. Bartony, Jr.

(57) ABSTRACT

A system for injection of a fluid into a body includes: a source of a first fluid, a source of a second fluid; the first fluid being less toxic than the second fluid; at least one pressurizing system in operative connection with the source of the first fluid and with the source of the second fluid; at least one controller in operative connection with the pressurizing system; and at least a first sensor in communicative connection with the controller. The first sensor is adapted to transmit a signal of a detected change in fluid level in tissue indicative of extravasation to the controller. The controller is adapted to cause injection of the first fluid into the body to determine if extravasation of the first fluid occurs using the sensor in an administration phase before injection of the second fluid.

23 Claims, 4 Drawing Sheets

U.S. PATENT DOCUMENTS

| | | |
|---|---|---|
| 2003/0036674 A1 | 2/2003 | Bouton |
| 2003/0036713 A1 | 2/2003 | Bouton et al. |
| 2004/0064041 A1 | 4/2004 | Lazzaro et al. |
| 2004/0176690 A1 | 9/2004 | Brabrand |
| 2004/0215081 A1 | 10/2004 | Crane et al. |
| 2005/0113754 A1 | 5/2005 | Cowan |

FOREIGN PATENT DOCUMENTS

| | | |
|---|---|---|
| WO | 03009753 | 2/2003 |
| WO | 05043100 | 5/2005 |

* cited by examiner

DEVICES, SYSTEMS AND METHODS FOR DETECTING INCREASE FLUID LEVELS IN TISSUE

BACKGROUND OF THE INVENTION

The present invention relates generally to the devices, systems and methods of detecting increased fluid levels in tissue, and particularly to devices, systems and method of detecting increased fluid levels associated with extravasation in tissues and controlling powered injectors in response to such detection.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

Elevated fluid levels in tissue can arise as a result of introduction of a fluid into the body, for example, during an injection procedure. In that regard, in many medical diagnostic and therapeutic procedures, a physician or other person injects fluid into a patient and, particularly, into a patient's blood vessels. Moreover, in recent years, a number of injector-actuated syringes and powered injectors for pressurized injection of contrast medium in procedures such as angiography, computed tomography, ultrasound and NMR/MRI have been developed. Such pressurized injectors can also be use in the delivery of therapeutic agents.

Extravasation or infiltration is the accidental infusion or leakage of an injection fluid such as a contrast medium or a therapeutic agent into tissue surrounding a blood vessel rather than into the blood vessel itself. Extravasation can be caused, for example, by rupture or dissection of fragile vasculature, valve disease, inappropriate needle placement, or patient movement resulting in the infusing needle being pulled from the intended vessel or causing the needle to be pushed through the wall of the vessel. High injection pressures and/or rates of some modem procedures can increase the risk of extravasation. In computed tomography, for example, contrast injection flow rates can be in the range of 0.1 to 10 ml/s.

Extravasation can cause serious injury to patients. In that regard, certain injection fluids such as contrast media or chemotherapy drugs can be toxic to tissue. It is, therefore, very important when performing fluid injections to detect extravasation as soon as possible and discontinue the injection upon detection.

Several extravasation detection techniques are known in the art. Two simple and very useful techniques for detecting extravasation are palpation of the patient in the vicinity of the injection site and simple visual observation of the vicinity of the injection site by a trained health care provider. In the palpation technique, the health care provider manually senses swelling of tissue near the injection site resulting from extravasation. By visual observation, it is also sometimes possible to observe directly any swelling of the skin in the vicinity of an injection site resulting from extravasation.

In a procedure involving injection of a fluid that can cause significant harm if extravasation occurs, one can first inject a relatively benign fluid through the needle/catheter and determine if an extravasation of the relatively benign fluid occurs. Published U.S. Patent Application No. 2002/0183613, the disclosure of which is incorporated herein by reference, for example, discloses a method of preventing extravasation of a contrast agent during a computed tomography injection using an automatic injector device. The method includes the steps of establishing the absence of extravasation using an absorbable injectate, such as saline, prior to injecting the contrast agent. The automatic injector includes a computerized injector head capable of switching between two injectates without physical human intervention. During, the method an operator first attempts to position distal end of a percutaneous implement such as a catheter in the vessel such that fluid communication is established between the lumen of the catheter and the vessel. The injector is then instructed to inject saline through the catheter lumen. A determination is then made (via palpation/observation) if an extravasation of the saline has occurred. If it is determined that no extravasation has occurred, the injector is instructed to inject contrast agent. If an extravasation is determined to have occurred during the saline injection, the process steps of repeated positioning the catheter within the blood vessel, injection saline and determining if an extravasation of saline has occurred are repeated.

In addition to palpation and observation, there are a number of automated methods of detecting extravasation that may include automatic triggering of an alarm condition upon detection.

In that regard, several plethysmographic detection techniques are available. For example, mercury strain gauge plethysmographs measure the volume change resulting from venous blood flow in a cross sectional area of a limb of a patient. Air cuff or pulse volume recorder plethysmographs measure the changes in pressure within a recording cuff. Such plethysmographs can be cumbersome to operate and/or insensitive to small changes in volume.

Impedance plethysmographs use low-frequency electromagnetic energy transmitted via galvanic contact with the skin to measure changes in the electrical impedance in a defined tissue volume of a limb. Detection of extravasation via impedance changes is disclosed, for example, in U.S. Pat. Nos. 5,964,703 and 5,947,910, the disclosures of which are incorporated herein by reference. In this method, an impedance change of a certain level relative to a baseline measurement in the vicinity of the injection site is interpreted as being an extravasation. A change in impedance occurs during extravasation because injection fluid in the tissue of the patient changes both the volume and the electrical impedance properties of the tissue. Use of electrodes in impedance plethysmographs can, however, result in instabilities. For example, maintaining suitable electrical (ohmic or galvanic) contact between the electrodes of impedance plethysmographs and the skin of the patient is often very difficult.

Photo-plethysmographs measure the optical scattering properties of capillary blood to detect the presence of extravasated fluids in tissue. An example of a photo-plethysmograph is described in U.S. Pat. No. 4,877,034, the disclosure of which is incorporated herein by reference. Because light is heavily absorbed in tissue, however, the sensitivity of photo-plethysmographs is generally limited to the top ¼ inch of tissue. Many extravasations, however, occur deeper than ¼ inch. Moreover, the injection medium may flow into interstitial spaces remote from the photoplethysmograph sensors and go undetected.

A number of extravasation detection devices attempt to measure temperature differences to determine if an extravasation has occurred. For example, U.S. Pat. No. 4,647,281 discloses subcutaneous temperature sensing of extravasation to trigger an alarm. In this method of extravasation detection, an antenna and a microwave radiometer instantaneously measure the temperature of the subcutaneous tissue at the site where fluid is injected by measuring microwave radiation emitted naturally from the body. An algorithm periodically determines the temperature difference between tissue and injected fluid, and compares the difference to a fixed threshold. An alarm processor uses the comparison to determine an alarm condition.

In addition, U.S. Pat. No. 5,334,141, the disclosure of which is incorporated herein by reference, discloses a microwave extravasation detection system employing a reusable microwave antenna and a disposable attachment element for releasably securing the microwave antenna to a patient's skin over an injection site. The attachment element holds the antenna in intimate contact with the patient's skin to optimize microwave transfer therebetween, while shielding the antenna from environmental noise signals. U.S. Pat. No. 5,954,668, the disclosure of which is incorporated herein by reference, also discloses use of a microwave antenna to sense temperature of tissue to detect extravasation. Although measurement of temperature changes and emissivity using microwave energy can result in instantaneous detection, temperature differences are often too small for practical measurement.

Published U.S. Patent Application Publication Nos. 2003/0036674 and 2003/0036713 and Published PCT International Patent Application Nos. WO/2003/009753, WO/2003/009752 and WO 2005/043100, assigned to the assignee of the present invention, the disclosures of which are incorporated herein by reference, disclose transmitting and receive antenna elements, sensing methods and processing algorithms suitable for the detection of elevated fluid levels (including those caused by extravasation) using active transmission of microwave energy into tissue. The studies of sensors incorporating such antenna elements have shown that electromagnetic energy having, for example, a frequency in the range of approximately 300 MHz to approximately 30 GHz (and, more preferably, in the range of approximately 1 GHz to approximately 10 GHz, and, even more preferably, in the range of approximately 3 GHz to approximately 5 GHz) provides good penetration into tissue. Such electromagnetic energy is launched into the subcutaneous tissue and a resultant signal is measured. Electromagnetic energy in the frequency range set forth above has been found to transmit through the skin and to transmit or propagate well within, for example, fat. Good transmission through the fat layer is beneficial for detection of extravasation as many extravasations occur in the fat layer.

It is desirable to develop improved devices, systems and methods of detecting and preventing extravasation.

SUMMARY OF THE INVENTION

In one aspect, the present invention provides a system for injection of a fluid into a body, including: a source of a first fluid, a source of a second fluid; the first fluid being less toxic than the second fluid; at least one pressurizing system in operative connection with the source of the first fluid and with the source of the second fluid; at least one controller in operative connection with the pressurizing system; and at least a first sensor in communicative connection with the controller. The first sensor is adapted to transmit a signal of a detected change in fluid level in tissue indicative of extravasation to the controller. The controller is adapted to cause injection of the first fluid into the body to determine if extravasation of the first fluid occurs using the sensor in an administration phase before injection of the second fluid.

The controller can, for example, inject the first fluid into the body in a manner to approximate at least one parameter of at least one phase of injection of the second fluid programmed in the controller. For example, the first fluid can be injected at a rate simulating on or more predetermined rates of the subsequent injection of the second fluid. The flow rate of the first fluid can also be varied during the administration phase.

The first fluid can, for example, be saline or another relatively harmless, benign or nontoxic fluid. The second fluid can, for example, include a contrast medium for use in connection with an imaging procedure. The second fluid alternatively or additionally include a therapeutic agent.

In one embodiment, the pressurizing system includes an injector including at least a first drive member and a second drive member. The source of the first fluid can, for example, be a first syringe having a plunger slidably disposed therein, and the source of the second fluid can, for example, be a second syringe having a plunger slidably disposed therein. The injector can include a first interface adapted to attach the first syringe thereto and a second interface adapted to attach the second syringe thereto. The first drive member can be adapted to cooperate with the plunger of the first syringe and the second drive member can be adapted to cooperate with the plunger of the second syringe.

The first sensor can, for example, include at least one transmitting antenna and at least one receiving antenna. The transmitting antenna can be adapted to transmit electromagnetic energy in the frequency range of approximately 300 MHz to approximately 30 GHz into a first volume of the body and the receiving antenna being adapted to receive a resultant signal. The resultant signal can be proportional to permittivity changes in the first volume of the body.

The system can further include at least a second sensor in communicative connection with the controller. The second sensor is adapted to transmit a signal of a detected change in fluid level in tissue indicative of extravasation to the controller. The second sensor preferably operates in a different manner than the first sensor. For example, the first sensor can operate by detecting permittivity changes in tissue (or in another manner), while the second sensor can operate by, for example, detecting changes in volume, temperature, conductivity, light transmissivity, impedance etc.

In another aspect, the present invention provides a method of injecting a fluid into a body, including: providing a source of a first fluid; providing a source of a second fluid, the first fluid being less toxic than the second fluid; providing at least one pressurizing system in operative connection with the source of the first fluid and with the source of the second fluid; providing at least one controller in operative connection with the pressurizing system; placing at least a first sensor in operative connection with the body; placing the first sensor in communicative connection with the controller, the first sensor being adapted to transmit a signal of detected changes in tissue fluid level indicative of extravasation to the controller; injecting the first fluid into the body in an administration phase; determining if an extravasation of the first fluid occurs using the first sensor during the administration phase; and communicating any extravasation detected by the first sensor to the controller.

The method can further include the step of injecting the second fluid into the body if no extravasation is detected by the first sensor during injection of the first fluid in the administration phase. As described above, the controller can, for example, inject the first fluid into the body in a manner to approximate at least one parameter of at least one phase of injection of the second fluid programmed in the controller. As also described above, the pressurizing system can include an injector including at least a first drive member and a second drive member.

The first sensor can include at least one transmitting antenna and at least on receiving antenna. The transmitting antenna can be adapted to transmit electromagnetic energy in the frequency range of approximately 300 MHz to approximately 30 GHz into a first volume of the body, and the receiving antenna can be adapted to receive a resultant signal. The resultant signal can be proportional to permittivity changes in the first volume of the body.

The method can further include the steps of placing at least a second sensor in operative connection with the body and placing the second sensor in communicative connection with the controller. The second sensor is adapted to transmit a signal of a detected change in fluid level in tissue indicative of extravasation to the controller. The second sensor preferably operates in a different manner than the first sensor.

The method can further include the step of reestablishing an injection site in the body if extravasation is detected in the administration phase.

BRIEF DESCRIPTION OF THE DRAWINGS

The invention, and particularly its presently preferred and alternative embodiments and related aspects, will be better understood by reference to the detailed disclosure below and to the accompanying drawings, in which.

DETAILED DESCRIPTION OF THE INVENTION

In several embodiments, the present invention provides a closed-loop technique for determining the stability of an injection site by administering a relatively nontoxic, harmless or benign first fluid (for example, saline) to a patient while monitoring the injection site with an extravasation sensor. This administration step occurs prior to the injection of a second fluid, for example, a therapeutic or diagnostic bolus of a drug. If the first fluid (for example, saline) is determined to extravasate into the tissue, the first fluid is less toxic than the second fluid to be injected and is likely to cause complications as a result of the extravasation.

Figure 1:
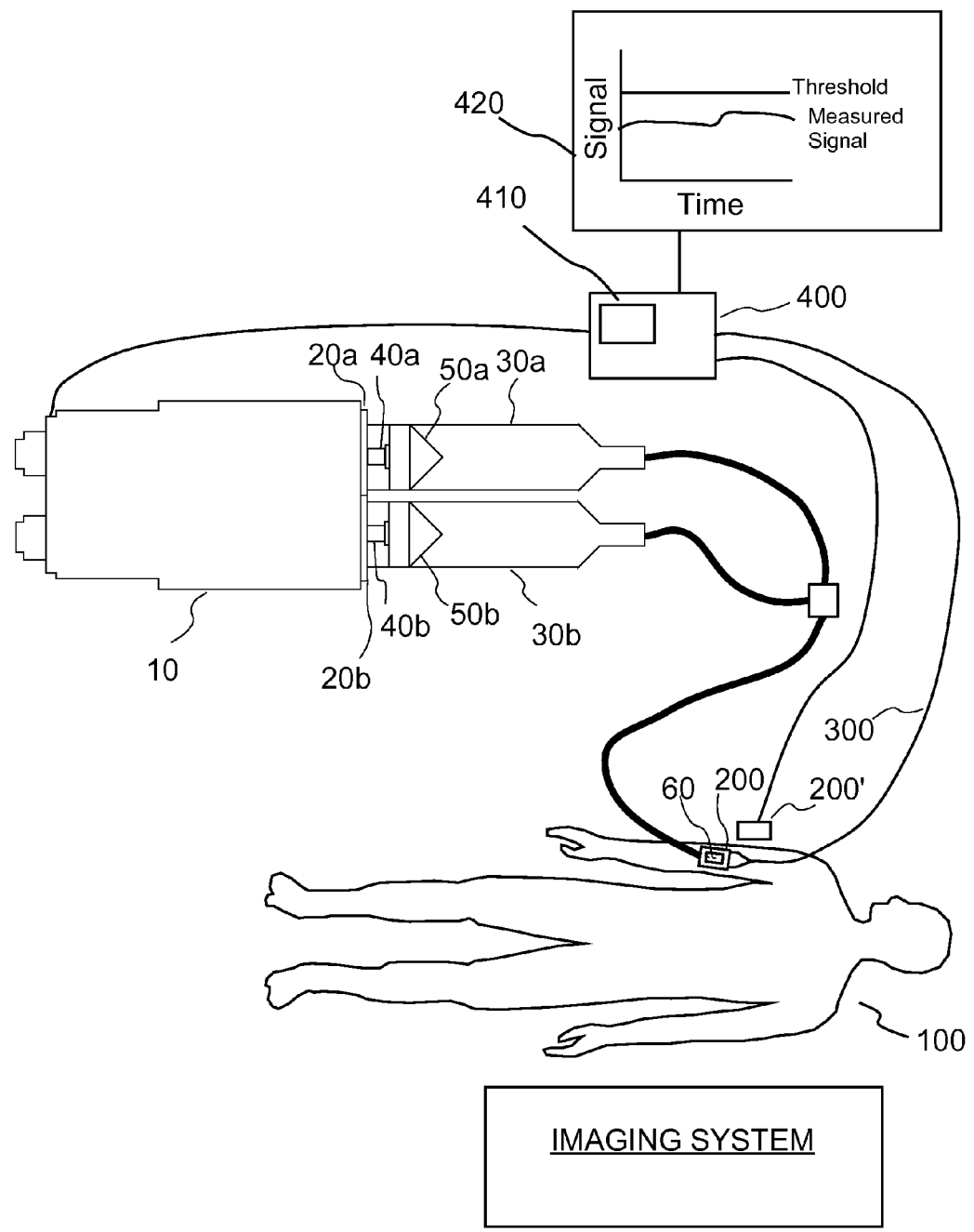
FIG. 1 illustrates a system of the present invention in which an extravasation sensor sends a feedback signal to a controller of an injector system during an imaging procedure.

As illustrate in FIG. 1, one embodiment of an injection system of the present invention includes an injector 10 such as the STELLANT® injector available from Medrad, Inc. of Indianola, Penn. Injector 10 includes two syringe interfaces 20a and 20b to which two syringes 30a and 30b are removably attachable. Two drive members or pistons 40a and 40b operatively connect to plungers 50a and 50b slidably disposed in syringes 30a and 30b, respectively, to pressurize and inject the fluid therefrom into a patient 100 via a catheter 60 in fluid connection with syringes 30a and 30b. Such injectors, control systems therefor and injector protocols used therewith are described, for example, in U.S. Pat. Nos. 6,643,537, 6,339,718, 6,958,053 and 5,494,036 and in Published U.S. Patent Application Nos. 2004-0064041, 2005-0113754, the disclosures of which are incorporated herein by reference.

The system of FIG. 1 further includes an extravasation sensor 200. Suitable sensors for use in the present invention include, but are not limited to, the fluid level/extravasation sensors disclosed in Published U.S. Patent Application Publication Nos. 2003/0036674 and 2003/0036713 and Published PCT International Patent Application Nos. WO/2003/009753, WO/2003/009752 and WO 2005/043100. Such sensors actively transmit electromagnetic energy (for example, microwave energy) into the subcutaneous tissue of patient 100 and measure a resultant signal.

In that regard, complex permittivity and permeability govern how an electromagnetic wave will propagate through a substance such as subcutaneous tissue. Complex permittivity typically has the greatest effect since it varies significantly between tissue types and fluids of interest. The complex permeability of various tissues and many fluids of interest is approximately that of a vacuum, reducing the effect of this parameter. Some fluids, however, such as water, saline solution and contrast agents can have an appreciable complex permittivity difference from tissue. Although blood contains small amounts of iron, the permeability value for any significant volume of blood is typically insignificant. Complex permittivity is generally expressed as:

$$\epsilon^* = \epsilon' - j\epsilon''$$

wherein $\epsilon'$ is the real component of the complex value and is known as the dielectric constant or sometimes simply referred to as the "permittivity." The term "$\epsilon''$" is the imaginary component of the complex value and is often referred to as the "loss factor." The ratio of ($\epsilon''/\epsilon'$) is known as the "loss tangent." The complex permittivity (and sometimes permeability) of certain substances differ from the body tissue at certain frequencies. In the sensors of Published U.S. Patent Application Publication Nos. 2003/0036674 and 2003/0036713 and Published PCT International Patent Application Nos. WO/2003/009753, WO/2003/009752 and WO 2005/043100, such differences in permittivity and/or permeability are used for the detection and level monitoring of fluids and substances in biological tissue. Studies of such sensors have shown that electromagnetic energy having, for example, a frequency in the range of approximately 300 MHz to approximately 30 GHz (and, more preferably, in the range of approximately 1 GHz to approximately 10 GHz, and, even more preferably, in the range of approximately 3 GHz to approximately 5 GHz) provides good penetration into tissue.

Figure 2:
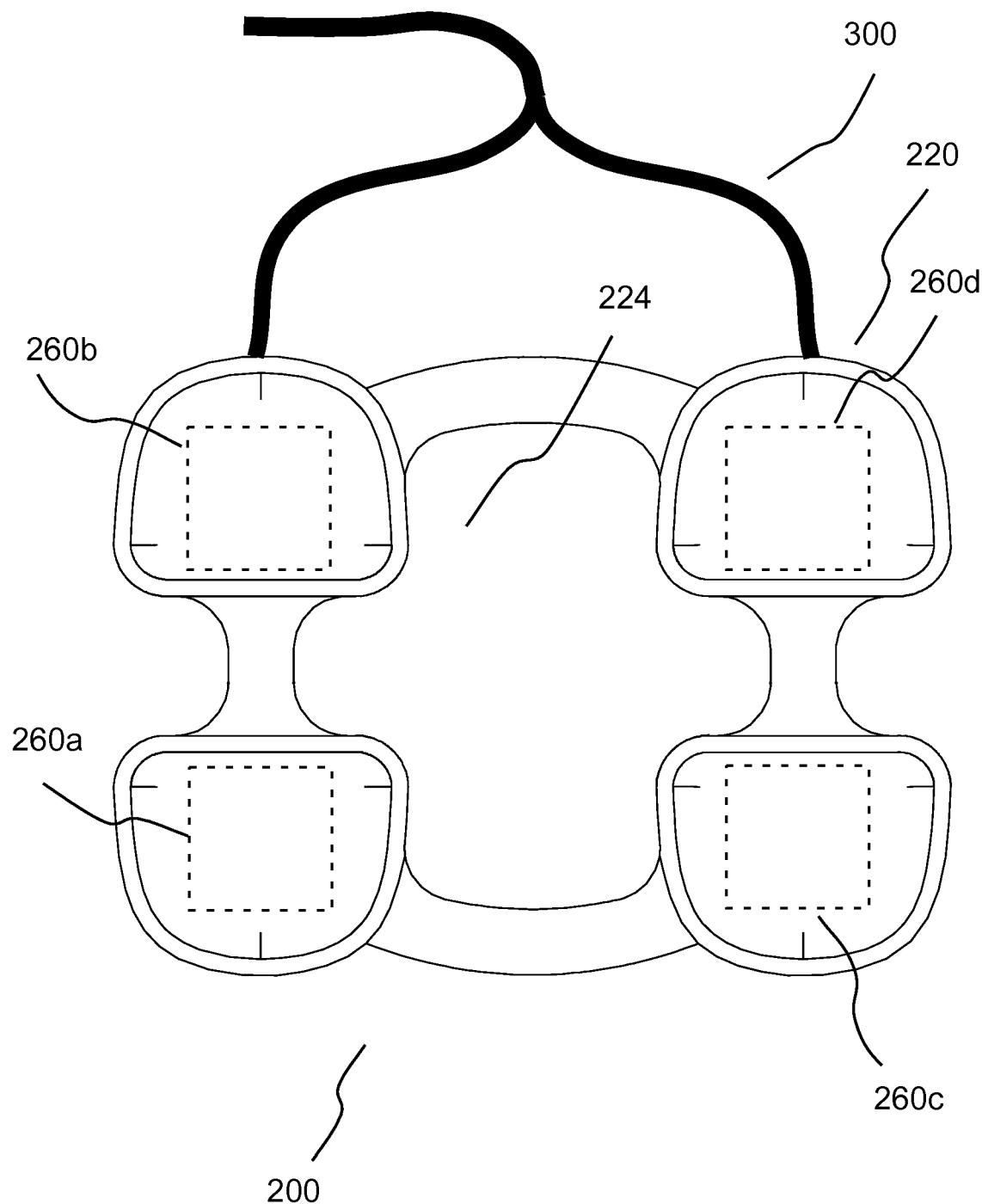
FIG. 2 is a top view of an embodiment of an extravasation sensor suitable for use in the present invention.

FIG. 2 illustrates a top view of one embodiment of extravasation sensor 200 for use in the present invention. Extravasation sensor 200 includes a housing 220, a plurality of antenna or sensor elements 260a, 260b, 260c and 260d, and the RF cable assembly(ies) 300 associated therewith. Housing 220 can, for example, be fabricated from a base material, such as urethane and/or silicone material. A ferromagnetic and/or other material suitable to absorb leakage of electromagnetic energy can be mixed into the base material. A carbonyl iron powder, such as the EW grade carbonyl iron powder produced by the BASF Corporation, of Mount Olive, N.J., is suitable for this purpose. The ferromagnetic powder can be mixed into the housing base material at least around the antenna elements and cables. A ferromagnetic material with appreciable permeability (e.g., >1), such as the EW grade carbonyl iron powder, provides a mixture that creates a flexible housing capable of absorbing stray leakage of electromagnetic energy. If not effectively addressed, such leakage could potentially cause artifacts to be induced within the signals conveyed from the antenna elements as a result of, for example, palpation of the skin in the area of the extravasation sensor 200 or as a result of other movement of the sensor 200. In addition to motion and palpation artifacts, such leakage could also decrease the sensitivity of the sensor 200 to the presence of subcutaneous fluid. It is apparent that one can also mix the ferromagnetic material into a different base material (for example, a base material that will form a more rigid housing).

Housing 220 of the extravasation sensor 200 can, for example, define an opening 224 between the antenna elements 260a-d. Opening 224 provides both visual and tactile (palpation) access to the site of interest where subcutaneous fluid will likely accumulate should extravasation occur. Opening 224 thus provides the operator with the option of checking for or confirming the presence of fluid merely by looking at or palpating the skin through opening 224 in housing 220.

Cabling 300 can, for example, be used to provide a signal from sensor 200 to a control system 400 in operative connection with injector 10. As known in the art, control system 400 can be positioned in a control room (not shown) to protect an operator from, for example, X-ray energy used in a CT scan. Control system 400 or a portion thereof can additionally or alternatively be located in proximity to injector 10 or integrated therewith.

Antennae 260a and 260b can, for example, form a first antenna pair, while antennae 260c and 260d can form a second antenna pair. In the first antenna pair, antenna 260a can, for example, operate as a first transmitting antenna and antenna 260b can operate as a first receiving antenna. In the second antenna pair, antenna 260c can, for example, operate as a second transmitting antenna and antenna 260d can include a second receiving antenna. As described, for example, in Published U.S. Patent Application Publication Nos. 2003/0036674 and 2003/0036713 and Published PCT International Patent Application Nos. WO/2003/009753, WO/2003/009752 and WO 2005/043100, the first antenna pair and the second antenna pair are placed in spaced contact with the patient. Electromagnetic energy (for example, in the frequency range of approximately 300 MHz to approximately 30 GHz) is transmitted into the patient's tissue via the first transmitting antenna and the second transmitting antenna. Resultant signals from the first receiving antenna and the second receiving antenna are transmitted to control system 400. The signals can be compared using a processor 410 of controller 400 (for example, a microprocessor as known in the art) to a reference to determine if permittivity/fluid level in the tissue has changed during the period of time, indicating an extravasation.

One or more displays 420 can be provided within the field of view of one or more operators to provide a representation of a signal received from extravasation sensor 200 (for example, a measure of permittivity) to provide for operator intervention during the saline injection/extravasation detection administration step and during the subsequent injection of the drug. Likewise, as described above, opening 224 in sensor 200 and other sensors can provide observation and/or palpation the skin to manually confirm the presence or absence of extravasation.

Once again, connection of an automated extravasation sensor such as sensor 200 in communicative connection with control system 400 of injector 10 provides for a closed-loop technique to determine the stability of an injection site by, for example, administering saline while monitoring the site with automatic sensor 200. In general, any type of automated sensor suitable to detect changes in fluid levels in tissue can be used in connection with the systems of the present invention. Sensors for the detection of extravasation are, for example, disclosed in U.S. Pat. Nos. Re38,879, RE38,695, 6,751,500, 6,487,428, 6,459,931, 6,425,878, 6,408,204, 6,375,624, 5,964,703, 5,954,668, 5,947,910, 5,334,141, and 4,877,034 as well as those disclosed in Published U.S. Patent Application Publication Nos. 2004/0215081, 2004/0176690, 2003/0004433, 2003/0036674, 2003/0036713, and 2002/0172323 and Published PCT International Patent Application Nos. WO/2003/009753, WO/2003/009752 and WO 2005/043100, the disclosures of which are incorporated herein by reference. The saline/extravasation detection administration step preferably occurs prior to the injection of the diagnostic, therapeutic or other bolus of drug. If saline extravasates into the tissue for any reason, the saline is less toxic than the drug and thus less likely to cause complications.

The preliminary saline injection/extravasation detection administration step can include injection of saline using an injection protocol that simulates one or more parameters of the injection protocol (which can, for example, include a one or more phases) set for the injection of the diagnostic, therapeutic or other drug. For example, the injection rate of saline from, for example, syringe 30a can be approximately the same as the injection rate (or, for example, the maximum injection rate) of the drug. Likewise, the injection rate of saline can be ramped or otherwise changed over the course of the saline injection/extravasation detection administration step to simulate the injection of the drug from syringe 30b in one or more phases of drug delivery. Depending upon the nature of the data received from extravasation sensor 200, controller 400 can, for example, extend the period of the saline injection/extravasation detection administration step or change the parameters thereof (for example, injection rate). In that regard, if data received by controller 400 from extravasation sensor 200 is inconclusive as to whether an extravasation has occurred the saline injection/extravasation detection administration step can be extended.

Various models or protocols can be used to determine if an extravasation has occurred. In an example, a binary hypothesis detection model is used where $H_0$ is the hypothesis condition when no event (extravasation) occurs and $H_1$ is the hypothesis condition when an extravasation is present.

$$H_1: m+n(t)$$

$$H_0: n(t) \quad (0.1)$$

It is assumed at each instant of time, a sample is recorded by the processing system. The observation is designated $r_i$. The observation r is a random variable having the value of one of the two hypotheses.

Figure 3:
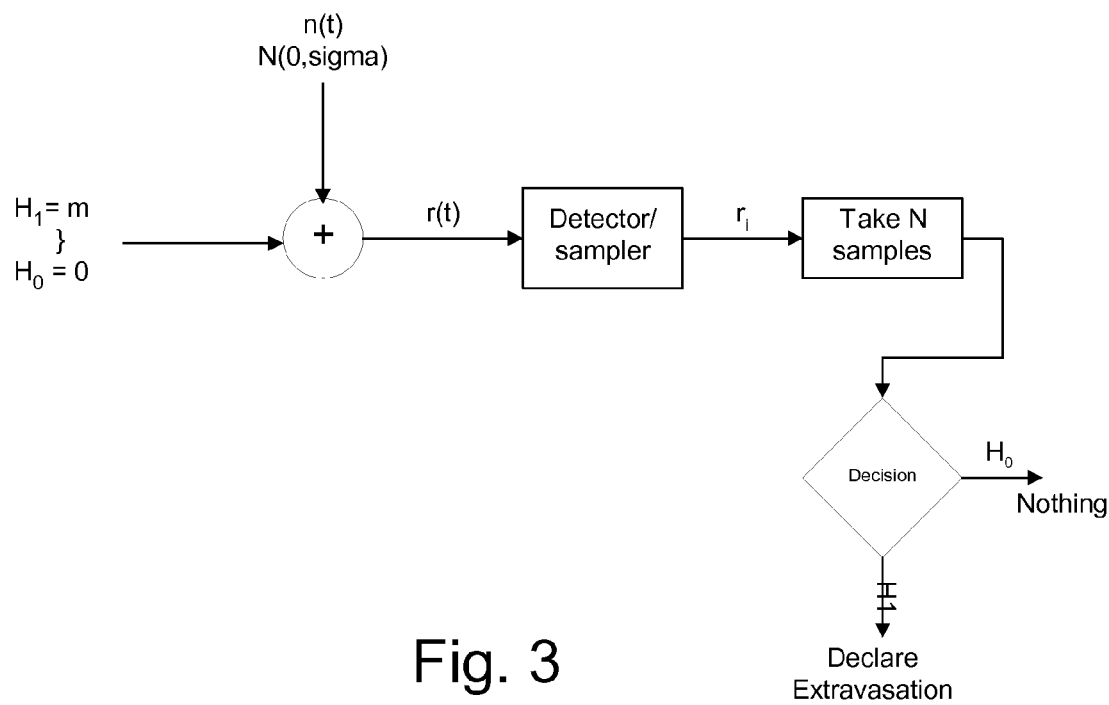
FIG. 3 illustrates a block diagram of a binary detection model assuming that an extravasation event can be characterized as a constant offset.

The model assumes that when an extravasation occurs, a shift in the sensor signal's magnitude occurs. This shift holds a constant value, m, while the $H_1$ hypothesis is true. This model is illustrated in FIG. 3. It is also possible to treat the signal change as time dependent and having its own probability distribution.

The function n(t) is assumed to be an ensemble of independent and identically distributed (i.i.d), normal, random variables, the value of which differs for each observation instant. Eq 0.1 can now be recast in terms of the observed random signal as follows:

$$H_1: r_i = m+n_i$$

$$H_0: r_i = n_i \quad (0.2)$$

Figure 4:
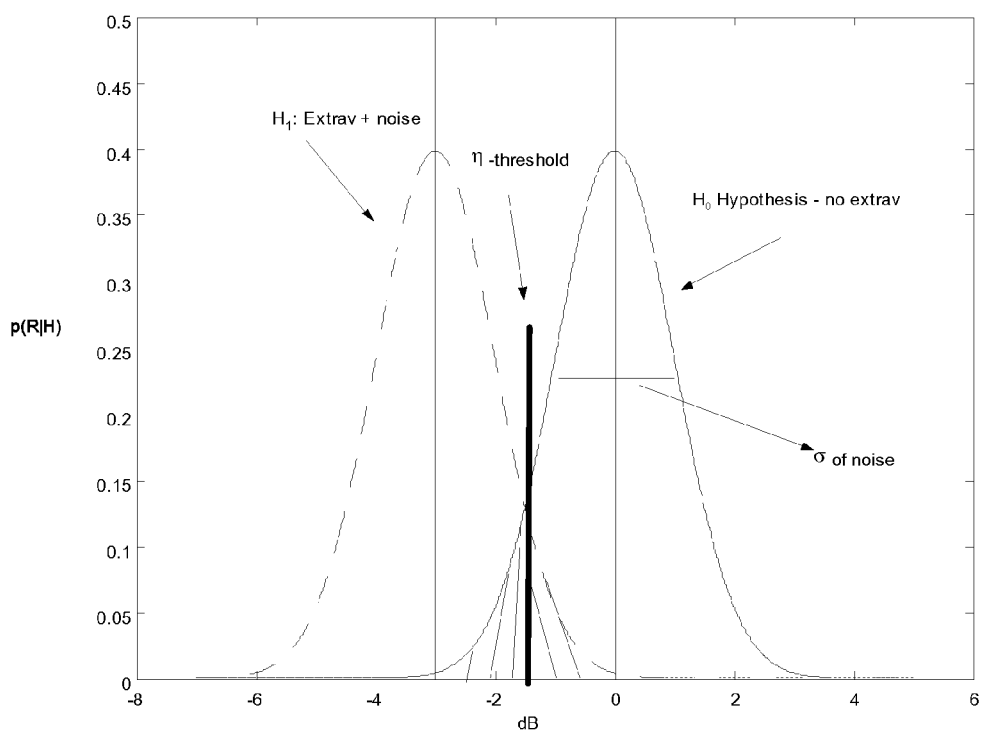
FIG. 4 illustrates probability density functions for an $H_1$ hypothesis (extravasation plus noise) and an $H_0$ hypothesis (no extravasation).

It is assumed that one can take N samples of the observed signal, r. It is also assumed that the noise disturbance can be modeled as a Gaussian process and that the process is zero mean (that is, the system has a method of subtracting the baseline from the sensor reading). The scenario can be visualized as depicted in FIG. 4.

Further assuming that the noise distribution is the same under both distributions, one can express the conditional probabilities of the two hypotheses (for a single observation) as:

$$H1:\ p(R_i\mid H_i) = \frac{1}{\sqrt{2\pi}\,\sigma} e^{\frac{-(R_i-m)^2}{2\sigma^2}} \quad (0.3)$$

$$H0:\ p(R_i\mid H_0) = \frac{1}{\sqrt{2\pi}\,\sigma} e^{\frac{-R_i^2}{2\sigma^2}} \quad (0.4)$$

In the case in which one makes multiple measurements (as depicted in FIG. 3), and assuming statistical independence of the noise, one can express the probability densities as products of Gaussian random variables:

$$p(R\mid H_1) = \prod_{i=1}^{N} \frac{1}{\sqrt{2\pi}\,\sigma} e^{\frac{-(R_i-m)^2}{2\sigma^2}} \quad (0.5)$$

$$p(R\mid H_0) = \prod_{i=1}^{N} \frac{1}{\sqrt{2\pi}\,\sigma} e^{\frac{-R_i^2}{2\sigma^2}} \quad (0.6)$$

One can define a Likelihood Ratio Test as the ratio of the two probability densities in 0.5 and 0.6

$$\Lambda(R) = \frac{\prod_{i=1}^{N} \frac{1}{\sqrt{2\pi}\,\sigma} e^{\frac{-(R_i-m)^2}{2\sigma^2}}}{\prod_{i=1}^{N} \frac{1}{\sqrt{2\pi}\,\sigma} e^{\frac{-R_i^2}{2\sigma^2}}} \quad (0.7)$$

If one expands the exponentials in Eq.0.7 (the product of exponentials becomes exponential with summation of arguments) and cancels common terms, taking a logarithm of both sides (generating a log likelihood function—the log is a positive function), one arrives at the following:

$$\ln\Lambda(R) = \frac{m}{\sigma^2}\sum_{i=1}^{N} R_i - \frac{Nm^2}{2\sigma^2} \quad (0.8)$$

Figure 5:
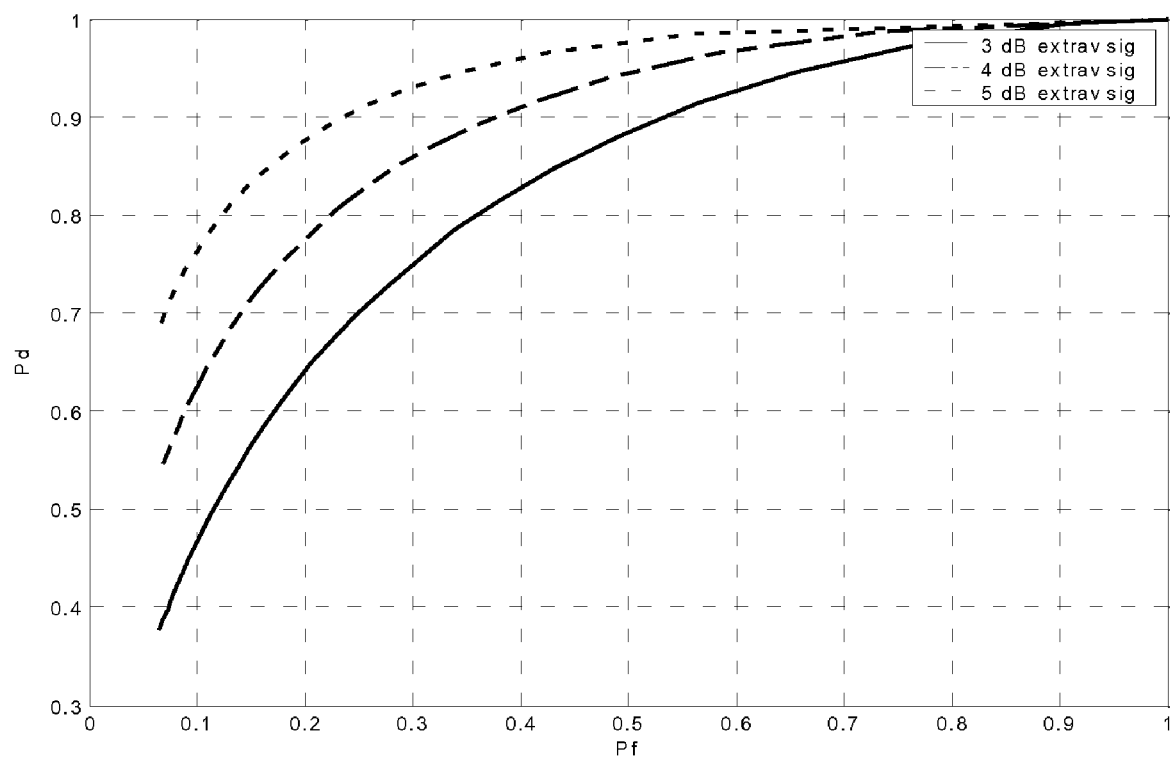
FIG. 5 illustrates receiver operator characteristics (ROCs). of an extravasation sensor as illustrated FIG. 2 resulting from observed data.

A threshold can be set somewhere between the two distributions as illustrated in FIG. 5. The probability (integral under the curve to the right of the threshold—cross hatched to the left in FIG. 4) of the $H_0$ hypothesis to the left of the threshold line can be established as the probability of declaring a no event when an extravasation actually occurs (that is, the probability of false alarm—$P_F$). The area under the $H_1$ probability density function to the left of the threshold line defines the probability of detection ($P_D$).

Recasting Eq. 0.8 by incorporating the threshold value, and bringing the data term (summation of Rs) to the left hand side, one can express a threshold test as:

$$\frac{1}{\sqrt{N}\,\sigma}\sum_{i=1}^{N} R_i \underset{H0}{\overset{H1}{\gtrless}} \frac{\sigma}{\sqrt{N}\,m}\ln\eta + \frac{\sqrt{N}\,m}{2\sigma} \quad (0.9)$$

If one divides both sides of 0.9 by $\sigma/\sqrt{N}$m, explicitly stating the integrals as described above and recognizing that the one can use the complimentary error function (erfc) in numerical simulations to evaluate Gaussian expressions, one can derive expressions for $P_D$ and $P_F$, plot one with respect to the other and generate receiver operator characteristics (ROCs).

$$P_D = \mathrm{erfc}\left(\frac{\ln\eta}{\frac{\sqrt{N}\,m}{\sigma}} - \frac{\frac{\sqrt{N}\,m}{\sigma}}{2}\right) \quad (0.10)$$

$$P_F = \mathrm{erfc}\left(\frac{\ln\eta}{\frac{\sqrt{N}\,m}{\sigma}} + \frac{\frac{\sqrt{N}\,m}{\sigma}}{2}\right) \quad (0.11)$$

The ROC illustrated in FIG. 5 is based on a MATLAB script that assumes that the extravasation event is a positive shift from the baseline. A sigma was derived based on observational clinical data gathered with a "permittivity" sensor such as illustrated in FIG. 2. Three curves were plotted assuming that an extravasation occurs when the measured signal exceeds 3, 4, and 5 dB. Eta ($\eta$) was varied from 0 to 3.

Various learning algorithms can also be implemented in the systems of the present invention. In that regard, the operational history of the injection and detection device can be recorded to allow the system to become more sensitive to extravasations of saline by noting the condition of signals made during actual extravasations as, for example, validated by the user. The system can apply, for example, a different detection threshold for higher volumetric flow rates, or if more viscous contrast media were selected by the user.

In one example of an operational protocol with a system of the present invention, the clinician can first establish intravenous access when the patient is in the scan/procedure room or prior to the patient's entry into the scan/procedure room. The clinician can then set up multiple injection operations via one or more user interfaces. The first step can, for example, be a "test" injection of saline or other benign fluid. Following phases can include an identification or timing bolus (that is, a small volume of contrast for determination of patient specific responses to the drug), pump priming steps, and ultimately a full diagnostic/therapeutic injection protocol (that can include multiple phases as described, for example, in connection with the injectors and control systems described in U.S. Pat. Nos. 6,643,537, 6,339,718, 6,958,053 and 5,494,036 and in Published U.S. Patent Application Nos. 2004-0064041, 2005-0113754) of diagnostic or therapeutic material. The clinician can then attach an extravasation sensor (as, for example, illustrated in FIG. 2) which performs a calibration check. The operator can then remotely, or at the patient's side, arm the injection system and commence a patency/preliminary extravasation detection injection. The operator can palpate and/or visualize the injection site while the extravasation system monitors the tissue surrounding the IV access for the presence of unwanted fluid from an extravasation. As described above, the flow rate of the injection can be automatically or manually increased or decreased while the system monitors the site.

If no extravasation is detected during the preliminary extravasation detection administration step, the injector controller 400 proceeds to effect injection of the drug from second syringe 30b via injector 10. Extravasation sensor 200 continues to operate during injection of the drug to sense extravasation. If an extravasation is detected during the preliminary extravasation detection administration step, however, the procedure can be ceased. A new injection site can, for example, then be established. After appropriate patient preparation, the preliminary extravasation detection administration step is repeated.

In the case of use of sensor 200, which measures changes in permittivity in a volume of tissue, sensor 200 is quite sensitive to extravasation of either saline, contrast medium or other drugs. In the case of certain automatic extravasation sensors, however, sensitivity may be tuned to, for example, a contrast medium or other drug. In such cases, in may be desirable to adjust/tune the sensor or the measurement algorithms/circuitry to make the sensor more sensitive to, for example, saline. Such tuning can, for example, be applied in the preliminary extravasation detection administration step and the sensor and/or measurement algorithms/circuitry can be "returned" to detect extravasation of the contrast/drug in the subsequent steps or phase(s). Additionally or alternatively, a different fluid can be used in the preliminary extravasation detection administration step. In general, fluids that are less toxic than the drug to be delivered are used in the preliminary extravasation detection administration step. It is also possible to use a diluted mixture of saline (or other generally nontoxic diluents) and the drug in the preliminary extravasation detection administration step to increase the sensitivity of an extravasation sensor to an extravasation during the preliminary extravasation detection administration step.

The physiologically benign or nontoxic fluid used in the preliminary extravasation detection administration step can contain detection enhancement agents such as inert particles or other entities that assist in signal detection. The nontoxic fluid (and any signal enhancing components therein) can be irradiated by an electromagnetic energy source and monitored by a detector outside the tissue.

In addition to primary extravasation sensor 200, one or more additional or secondary extravasation sensors 200' can be provided to make another, independent determination of extravasation. Like the signal from extravasation sensor 200, the signal from extravasation sensor 200' is provided to control system 400 (for example, via a transmission wire or in a wireless manner). In the case of, for example, the use of saline in a preliminary extravasation detection administration step, a permittivity sensor as described above is very sensitive to an extravasation of saline. Detection enhancement agents can, for example, be added to the saline or other benign fluid to improve the sensitivity of secondary sensor 200' to an extravasation (for example, particles that absorb or scatter electromagnetic radiation, such as near infrared (nIR) light etc., can be added to saline).

Although the various embodiments and related aspects of the invention herein described and illustrated are presented primarily in the context of injection of contrast during CT and other imaging procedures (for example, positron emission tomography (PET), magnetic resonance imaging (MRI), magnetic resonance angiography (MRA) and ultrasound procedures), one skilled in the art understands that the invention may also be applied or adapted to other types of applications as well as a wide variety of therapeutic and other procedures (and, particularly, to PET and other procedures using radiopharmaceuticals as well as to toxic, chemotherapy oncology agents).

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A system for injection of a fluid into a body, comprising:
   a source of a first fluid;
   a source of a second fluid, the first fluid being less toxic than the second fluid;
   at least one pressurizing system in operative connection with the source of the first fluid and with the source of the second fluid;
   at least one controller in operative connection with the pressurizing system; and
   at least a first sensor in communicative connection with the controller, the first sensor being adapted to transmit a signal of a detected change in fluid level in tissue indicative of extravasation to the controller, the controller being adapted to cause injection of the first fluid into the body to determine if extravasation of the first fluid occurs using the sensor in an administration phase before injection of the second fluid, wherein the first sensor is based on electromagnetic energy and to measure extravasation of the first fluid in at least a first volume of the tissue,
   wherein the at least one controller includes an extravasation protocol associated therewith, the extravasation protocol comprising a first protocol wherein at least one of operation of the first sensor or application of a detection model is set to measure extravasation of the first fluid in the administration phase during injection of the first fluid and a second protocol wherein at least one of operation of the first sensor or application of the detection model is set to measure extravasation of the second fluid during subsequent injection of the second fluid,
   wherein settings in the first protocol are different than settings in the second protocol.

2. The system of claim 1 wherein the controller injects the first fluid into the body in a manner to approximate at least one parameter of at least one phase of injection of a second fluid programmed in the controller.

3. The system of claim 2 wherein the flow rate of the first fluid is varied during the administration phase.

4. The system of claim 1 wherein the first fluid includes saline.

5. The system of claim 1 wherein the second fluid includes a contrast medium for use in connection with an imaging procedure.

6. The system of claim 1 wherein the second fluid includes a therapeutic agent.

7. The system of claim 1 wherein the source of the first fluid is a first syringe having a plunger slidably disposed therein and the source of the second fluid is a second syringe having a plunger slidably disposed therein, the injector comprising a first interface adapted to attach the first syringe thereto and a second interface adapted to attach the second syringe thereto, a first drive member of the pressurizing mechanism being adapted to cooperate with the plunger of the first syringe and a second drive member of the pressurizing mechanism being adapted to cooperate with the plunger of the second syringe.

8. The system of claim 1 wherein the first sensor comprises at least one transmitting antenna and at least one receiving antenna, the transmitting antenna being adapted to transmit electromagnetic energy in the frequency range of approximately 300 MHz to approximately 30 GHz into the first volume of the body in the first protocol and the second protocol and the receiving antenna being adapted to receive a resultant signal.

9. The system of claim 8 wherein the first protocol and the second protocol are substantially the same and the resultant signal is proportional to permittivity changes in the first volume of the body.

10. The system of claim 1 further comprising at least a second sensor in communicative connection with the controller, the second sensor being adapted to transmit a signal of a detected change in fluid level in tissue indicative of extravasation to the controller, the second sensor operating in a different manner than the first sensor.

11. The system of claim 1 wherein the extravasation protocol further includes at least one learning algorithm.

12. A method of injecting a fluid into a body, comprising:
providing a source of a first fluid;
providing a source of a second fluid, the first fluid being less toxic than the second fluid;
providing at least one pressurizing system in operative connection with the source of the first fluid and with the source of the second fluid;
providing at least one controller in operative connection with the pressurizing system;
placing at least a first sensor in operative connection with the body;
associating an extravasation protocol with the controller, the extravasation protocol comprising a first protocol wherein at least one of operation of the first sensor or application of a detection model is set to measure extravasation of the first fluid in an administration phase during injection of the first fluid and a second protocol wherein of at least one of operation of the first sensor or application of the detection model is set to measure extravasation of the second fluid during subsequent injection of the second fluid;
placing the first sensor in communicative connection with the controller, the first sensor being adapted to transmit a signal indicative of extravasation to the controller;
injecting the first fluid into the body in the administration phase while operating the first sensor according to settings of the first protocol;
obtaining at least one signal from the first sensor during the administration phase;
determining if an extravasation of the first fluid occurs using the at least one signal from the first sensor during the administration phase and the detection model as set by the first protocol,
communicating any extravasation detected by the detection model to the controllers;
injecting the second fluid into the body if no extravasation is detected by the first sensor during injection of the first fluid in the administration phase, while operating the first sensor according to the settings of the second protocol;
obtaining at least one signal from the first sensor during the injection of the second fluid;
determining if an extravasation of the second fluid occurs using the at least one signal from the first sensor during injection of the second fluid and the detection model as set by second first protocol, and
communicating any extravasation detected by the detection model to the controller,
wherein settings in the first protocol are different than settings in the second protocol.

13. The method of claim 12 wherein the controller injects the first fluid into the body in a manner to approximate at least one parameter of at least one phase of injection of the second fluid programmed in the controller.

14. The method of claim 13 wherein the flow rate of the first fluid is varied during the administration phase.

15. The method of claim 12 wherein the first fluid includes saline.

16. The method of claim 12 wherein the second fluid includes at least one of a contrast medium for use in connection with an imaging procedure or a therapeutic agent.

17. The method of claim 12 wherein the pressurizing system comprises an injector comprising at least a first drive member and a second drive member.

18. The method of claim 17 wherein the source of the first fluid is a first syringe having a plunger slidably disposed therein and the source of the second fluid is a second syringe having a plunger slidably disposed therein, the injector comprising a first interface adapted to attach the first syringe thereto and a second interface adapted to attach the second syringe thereto, the first drive member being adapted to cooperate with the plunger of the first syringe and the second drive member being adapted to cooperate with the plunger of the second syringe.

19. The method of claim 12 wherein the first sensor comprises at least one transmitting antenna and at least one receiving antenna, the transmitting antenna being adapted to transmit electromagnetic energy in the frequency range of approximately 300 MHz to approximately 30 GHz into a first volume of the body in the first protocol and the second protocol and the receiving antenna being adapted to receive a resultant signal.

20. The method of claim 19 wherein the first protocol and the second protocol are substantially the same and the resultant signal is proportional to permittivity changes in the first volume of the body.

21. The method of claim 12 further comprising the steps of placing at least a second sensor in operative connection with the body and placing the second sensor in communicative connection with the controller, the second sensor being adapted to transmit a signal of a detected change in fluid level in tissue indicative of extravasation to the controller, the second sensor operating in a different manner than the first sensor.

22. The method of claim 12 further comprising the step of reestablishing an injection site in the body if extravasation is detected in the administration phase.

23. A system for injection of a fluid into a body, comprising:
a source of a first fluid;
a source of a second fluid, wherein the first fluid is different than the second fluid;
at least one pressurizing system in operative connection with the source of the first fluid and with the source of the second fluid;
at least one controller in operative connection with the pressurizing system;
at least a first sensor in communicative connection with the controller, wherein the first sensor is adapted to transmit a signal of a detected change in fluid level in tissue indicative of extravasation to the controller, wherein the controller is adapted to cause injection of at least the first fluid into the body to determine if extravasation of at least the first fluid occurs using the sensor in an administration phase before injection of at least the second fluid, wherein the first sensor is based on electromagnetic energy and measures extravasation of the at least first fluid in at least a first volume of the tissue, wherein the at least one controller includes an extravasation protocol associated therewith, wherein the extravasation protocol comprises a first protocol having at least one of operation of the first sensor or application of a detection model is set to measure extravasation of the at least first fluid in the administration phase during injection of the at least first fluid, and a second protocol having at least one of operation of the first sensor or application of the detection model is set to measure extravasation of the at least second fluid during subsequent injection of the at least second fluid, wherein the first protocol and second protocol are different.

* * * * *

UNITED STATES PATENT AND TRADEMARK OFFICE
CERTIFICATE OF CORRECTION

PATENT NO. : 7,674,244 B2
APPLICATION NO. : 11/419821
DATED : March 9, 2010
INVENTOR(S) : Kalafut et al.

It is certified that error appears in the above-identified patent and that said Letters Patent is hereby corrected as shown below:

IN THE SPECIFICATION

In Column 1, Line 42, delete "modem" and insert -- modern --, therefor.

In Column 5, Line 5, delete "body. and" and insert -- body and --, therefor.

In Column 5, Line 38, delete "(ROCs)." and insert -- (ROCs) --, therefor.

In Column 10, Line 8, delete " $\sigma/\sqrt{N}m,$ " and insert -- $\frac{\sigma}{\sqrt{Nm}},$ --, therefor.

IN THE CLAIMS

In Column 12, Lines 22-23, in Claim 1, delete "the pressurizing system" and insert -- the at least one pressurizing system --, therefor.

In Column 12, Lines 24-25, in Claim 1, delete "the controller" and insert -- the at least one controller --, therefor.

In Column 12, Line 25, in Claim 1, delete "the first sensor" and insert -- at least the first sensor --, therefor.

In Column 12, Line 27, in Claim 1, delete "to the controller, the controller" and insert -- to the at least one controller, the at least one controller --, therefor.

In Column 12, Line 28, in Claim 1, delete "adapted to cause injection" and insert -- adapted to cause an injection --, therefor.

In Column 12, Line 30, in Claim 1, delete "the sensor" and insert -- at least the first sensor --, therefor.

Signed and Sealed this
Twenty-fourth Day of July, 2012

David J. Kappos
*Director of the United States Patent and Trademark Office*

CERTIFICATE OF CORRECTION (continued)
U.S. Pat. No. 7,674,244 B2

In Column 12, Line 31, in Claim 1, delete "before injection of" and insert -- before an injection of --, therefor.

In Column 12, Lines 31-32, in Claim 1, delete "the first sensor" and insert -- at least the first sensor --, therefor.

In Column 12, Line 38, in Claim 1, delete "the first sensor" and insert -- at least the first sensor --, therefor.

In Column 12, Line 40, in Claim 1, delete "during injection of the" and insert -- during the injection of the --, therefor.

In Column 12, Line 42, in Claim 1, delete "the first sensor" and insert -- at least the first sensor --, therefor.

In Column 12, Line 44, in Claim 1, delete "during subsequent injection" and insert -- during the subsequent injection --, therefor.

In Column 12, Lines 45-46, in Claim 1, delete "wherein settings in the first protocol are different than settings in the second protocol" and insert -- wherein the first protocol comprises a first set of settings and the second protocol comprises a second set of settings, and wherein the first set of settings differ from the second set of settings --, therefor.

In Column 12, Line 47, in Claim 2, delete "the controller" and insert -- that at least one controller --, therefor.

In Column 12, Line 51, in Claim 3, delete "wherein the flow rate" and insert -- wherein a flow rate --, therefor.

In Column 12, Line 66, in Claim 7, delete "the pressurizing mechanism" and insert -- the at least one pressurizing system --, therefor.

In Column 13, Line 1, in Claim 7, delete "the pressurizing mechanism" and insert -- the at least one pressurizing system --, therefor.

In Column 13, Line 3, in Claim 8, delete "the first sensor" and insert -- at least the first sensor --, therefor.

In Column 13, Lines 7-8, in Claim 8, delete "first volume of the body" and insert -- first volume of the tissue --, therefor.

In Column 13, Lines 13-14, in Claim 9, delete "first volume of the body" and insert -- first volume of the tissue --, therefor.

CERTIFICATE OF CORRECTION (continued)
U.S. Pat. No. 7,674,244 B2

In Column 13, Lines 16-17, in Claim 10, delete "the controller" and insert -- the at least one controller --, therefor.

In Column 13, Line 17, in Claim 10, delete "the second sensor" and insert -- at least the second sensor --, therefor.

In Column 13, Line 19, in Claim 10, delete "the second sensor" and insert -- at least the second sensor --, therefor.

In Column 13, Line 31, in Claim 12, delete "the pressurizing system" and insert -- the at least one pressurizing system --, therefor.

In Column 13, Line 34, in Claim 12, delete "the controller" and insert -- the at least one controller --, therefor.

In Column 13, Line 36, in Claim 12, delete "the first sensor" and insert -- at least the first sensor --, therefor.

In Column 13, Line 39, in Claim 12, delete "during injection of" and insert -- during an injection of --, therefor.

In Column 13, Line 40, in Claim 12, delete "the first sensor" and insert -- at least the first sensor --, therefor.

In Column 13, Lines 42-43, in Claim 12, delete "during subsequent injection" and insert -- during a subsequent injection --, therefor.

In Column 13, Line 44, in Claim 12, delete "the first sensor" and insert -- at least the first sensor --, therefor.

In Column 13, Line 45, in Claim 12, delete "the controller" and insert -- the at least one controller --, therefor.

In Column 13, Line 45, in Claim 12, delete "the first sensor" and insert -- at least the first sensor --, therefor.

In Column 13, Line 46, in Claim 12, delete "the controller" and insert -- the at least one controller --, therefor.

In Column 13, Line 48, in Claim 12, delete "the first sensor" and insert -- at least the first sensor --, therefor.

In Column 13, Line 50, in Claim 12, delete "the first sensor" and insert -- at least the first sensor --, therefor.

In Column 13, Line 53, in Claim 12, delete "the first sensor" and insert -- at least the first sensor --, therefor.

In Column 13, Line 57, in Claim 12, delete "the controllers" and insert -- the at least one controller --, therefor.

In Column 13, Line 58, in Claim 12, delete "controllers;" and insert -- controller; --, therefor.

In Column 13, Line 59, in Claim 12, delete "the first sensor" and insert -- at least the first sensor --, therefor.

In Column 13, Line 59, in Claim 12, delete "during injection of" and insert -- during the injection of --, therefor.

In Column 13, Lines 60-61, in Claim 12, delete "the first sensor" and insert -- at least the first sensor --, therefor.

In Column 13, Line 63, in Claim 12, delete "the first sensor" and insert -- at least the first sensor --, therefor.

In Column 13, Line 66, in Claim 12, delete "the first sensor" and insert -- at least the first sensor --, therefor.

In Column 13, Line 67 – Column 14, Line 1, in Claim 12, delete "during injection of" and insert -- during the injection of --, therefor.

In Column 14, Line 4, in Claim 12, delete "the controller" and insert -- the at least one controller --, therefor.

In Column 14, Line 7, in Claim 13, delete "the controller" and insert -- the at least one controller --, therefor.

In Column 14, Line 11, in Claim 14, delete "the flow rate" and insert -- a flow rate --, therefor.

In Column 14, Lines 19-20, in Claim 17, delete "the pressurizing system" and insert -- the at least one pressurizing system --, therefor.

In Column 14, Line 31, in Claim 19, delete "the first sensor" and insert -- at least the first sensor --, therefor.

In Column 14, Line 33, in Claim 19, delete "the transmitting antenna" and insert -- the at least one transmitting antenna --, therefor.

In Column 14, Line 46, in Claim 21, delete "the second sensor" and insert -- at least the second sensor --, therefor.

CERTIFICATE OF CORRECTION (continued)
U.S. Pat. No. 7,674,244 B2

In Column 14, Line 47, in Claim 21, delete "the second sensor" and insert -- at least the second sensor --, therefor.

In Column 14, Line 47, in Claim 21, delete "the controller" and insert -- the at least one controller --, therefor.

In Column 14, Line 49, in Claim 21, delete "the controller" and insert -- the at least one controller --, therefor.

In Column 14, Lines 49-50, in Claim 21, delete "the second sensor" and insert -- at least the second sensor --, therefor.

In Column 14, Lines 64-65, in Claim 23, delete "the pressurizing system" and insert -- the at least one pressurizing system --, therefor.

In Column 14, Lines 66-67, in Claim 23, delete "with the controller" and insert -- with the at least one controller --, therefor.

In Column 15, Line 1, in Claim 23, delete "the first sensor" and insert -- at least the first sensor --, therefor.

In Column 15, Line 3, in Claim 23, delete "the controller" and insert -- the at least one controller --, therefor.

In Column 15, Line 4, in Claim 23, delete "the controller" and insert -- the at least one controller --, therefor.

In Column 15, Line 4, in Claim 23, delete "to cause injection" and insert -- to cause an injection --, therefor.

In Column 15, Line 6, in Claim 23, delete "the sensor" and insert -- at least the first sensor --, therefor.

In Column 15, Line 7, in Claim 23, delete "before injection" and insert -- before an injection --, therefor.

In Column 15, Line 9, in Claim 23, delete "the first sensor" and insert -- at least the first sensor --, therefor.

In Column 16, Line 2, in Claim 23, delete "the first sensor" and insert -- at least the first sensor --, therefor.

In Column 16, Line 5, in Claim 23, delete "during injection" and insert -- during the injection --, therefor.

In Column 16, Lines 6-7, in Claim 23, delete "the first sensor" and insert -- at least the first sensor --, therefor.

In Column 16, Lines 9-10, in Claim 23, delete "during subsequent injection" and insert -- during the subsequent injection --, therefor.